United States Patent
Faroon et al.

(10) Patent No.: US 11,990,947 B2
(45) Date of Patent: May 21, 2024

(54) METHOD AND SYSTEM FOR NON-ELECTRIC COMMUNICATION IN WATER TREATMENT PLANTS OR MEDICAL APPLIANCES

(71) Applicants: Fresenius Medical Care Deutschland GmbH, Bad Homburg (DE); FRESENIUS MEDICAL CARE AG & CO. KGAA, Bad Homburg (DE); VIVONIC GMBH, Sailauf (DE)

(72) Inventors: Yahya Faroon, Greven (DE); Patrick Bessler, Erlenbach (DE); Robert Lindemann, Wiesbaden (DE); Jonas Hellhund, Frankfurt (DE); Arne Peters, Bad Homburg (DE); Gerome Newport Fischer, Oberursel (DE)

(73) Assignees: FRESENIUS MEDICAL CARE DEUTSCHLAND GmbH, Bad Homburg (DE); FRESENIUS MEDICAL CARE AG & CO. KGAA, Bad Homburg (DE); VIVONIC GMBH, Sailauf (DE)

( * ) Notice: Subject to any disclaimer, the term of this patent is extended or adjusted under 35 U.S.C. 154(b) by 235 days.

(21) Appl. No.: 17/763,709

(22) PCT Filed: Sep. 25, 2020

(86) PCT No.: PCT/EP2020/076829
§ 371 (c)(1),
(2) Date: Mar. 25, 2022

(87) PCT Pub. No.: WO2021/058707
PCT Pub. Date: Apr. 1, 2021

(65) Prior Publication Data
US 2022/0321238 A1 Oct. 6, 2022
US 2023/0163863 A2 May 25, 2023

(30) Foreign Application Priority Data
Sep. 27, 2019 (DE) .................... 10 2019 126 086.8

(51) Int. Cl.
A61M 1/14 (2006.01)
C02F 1/44 (2023.01)
H04B 11/00 (2006.01)

(52) U.S. Cl.
CPC .............. *H04B 11/00* (2013.01); *C02F 1/441* (2013.01); *A61M 1/14* (2013.01); *A61M 2205/35* (2013.01); *C02F 2209/03* (2013.01)

(58) Field of Classification Search
CPC .. A61M 1/1656; A61M 2205/35; A61M 1/14; A61M 2205/3576; A61M 2205/3561; H04B 11/00; C02F 1/441; C02F 2209/03
See application file for complete search history.

(56) References Cited

U.S. PATENT DOCUMENTS

| | | | | |
|---|---|---|---|---|
| 5,282,488 | A | * | 2/1994 | Roth ........................ B67D 7/78 |
| | | | | 137/271 |
| 2003/0080059 | A1 | * | 5/2003 | Peterson ............. A61M 1/1668 |
| | | | | 210/194 |

(Continued)

FOREIGN PATENT DOCUMENTS

| DE | 320 09 189 | 9/1983 |
|---|---|---|
| DE | 40 37 600 | 6/1992 |

(Continued)

*Primary Examiner* — Daniel L Murphy
*Assistant Examiner* — Amie M Ndure
(74) *Attorney, Agent, or Firm* — Jacobson Holman PLLC

(57) ABSTRACT

The invention relates to a communications device for non-electric communication between fluidically interconnected devices, the communications device being designed to be mounted in a position in a fluidic overall system formed by the fluidically interconnected devices and to receive and/or emit non-electric signals, in particular in the form of pressure or sound signals, the non-electric signals being transmitted via a line that fluidically interconnects the devices. The invention further relates to a method for non-electric communication between fluidically interconnected devices, the non-electric communication taking place preferably by means of pressure and/or sound signals via at least one line that fluidically interconnects the devices.

15 Claims, 2 Drawing Sheets

(56) References Cited

U.S. PATENT DOCUMENTS

| | | | |
|---|---|---|---|
| 2011/0214504 A1* | 9/2011 | Bradley | G01L 19/14 |
| | | | 73/723 |
| 2014/0263064 A1* | 9/2014 | Jones | A61M 1/36222 |
| | | | 73/61.41 |
| 2015/0204807 A1* | 7/2015 | Kamen | A61M 60/113 |
| | | | 374/44 |
| 2017/0074706 A1* | 3/2017 | Heide | G01F 15/14 |
| 2017/0173262 A1* | 6/2017 | Veltz | G16H 20/17 |
| 2018/0031399 A1* | 2/2018 | Heide | G01F 1/58 |
| 2020/0405937 A1* | 12/2020 | Mallipalli | A61M 1/154 |
| 2021/0283322 A1* | 9/2021 | Heide | H10N 30/1071 |
| 2021/0308349 A1* | 10/2021 | Wyeth | A61M 1/1656 |

FOREIGN PATENT DOCUMENTS

| | | | | |
|---|---|---|---|---|
| DE | 199 33 411 | | 2/2001 | |
| DE | 100 47 849 | | 10/2001 | |
| DE | 10047849 C1 * | | 10/2001 | A61M 1/1656 |
| WO | WO 99/554651 | | 10/1999 | |

\* cited by examiner

METHOD AND SYSTEM FOR NON-ELECTRIC COMMUNICATION IN WATER TREATMENT PLANTS OR MEDICAL APPLIANCES

The present invention relates to a communication device, to a method, and to a system for non-electric communication in water preparation systems and/or medical devices.

The networking of a plurality of medical devices or treatment machines plays an increasing role in modern everyday clinical life. A plurality of treatment machines are typically used, for example, in larger dialysis centers that are typically connected to common supply lines at the building side or in water preparation systems. The efficiency of everyday clinical life could in particular profit in such applications from an improved networking of the individual treatment devices since the operation and/or the cleaning, the disinfection, or the maintenance of the individual treatment devices could in this manner be coordinated with one another and with the operating state of further connected devices.

However, special precautions in particular have to be taken with blood treatment machines to ensure that the patient safety of a patient connected to the fluid circuit of a blood treatment machine is not reduced by electric communication modules of the blood treatment machines. This fact is one of the main obstacles in the networking of treatment devices and in particular of blood treatment devices or dialysis machines.

It is thus the underlying object of the present invention to alleviate or even to fully eliminate the problems known from the prior art. It is specifically an object of the present invention to enable a safe and efficient communication between devices fluidically connected to one another such as treatment devices.

This object is achieved by a communication device in accordance with claim 1, by a method in accordance with claim 8, and by a system in accordance with claim 14. A further aspect of the invention relates to a kit for diagnosing a fluidic system in accordance with claim 7.

The key idea of the present invention is here the fact that the communication between different devices communicating fluidically with one another takes place non-electrically. The basic idea of the inventive solution thus comprises devices/units that are connected to one another via a fluid line that is conventionally only used for the transport of fluid communicating with one another over the line or the fluid conducted therein in a non-electric manner, for example by means of pressure pulses or switching signals. The invention comprises all fluidically connected devices, that is also the case that gas is conducted in the lines connecting the devices/units.

This provides the advantage that no additional communication lines or modules have to be provided. There is furthermore no risk for the patient from electrical power due to the communication. In addition, the non-electric communication is less susceptible to attacks from the outside in comparison with, for example, a communication of the units via a network.

A first aspect of the present invention relates to a communication device for the non-electric communication between devices fluidically connected to one another, with the communication device being adapted to be arranged in a position in a total fluidic system formed by the devices fluidically connected to one another and to receive and/or transmit non-electric signals, in particular in the form of pressure signals or sound signals, with the non-electric signals being transmitted over a line fluidically connecting the devices to one another.

It has proven to be advantageous if the communication device has a microphone and/or an ultrasound receiver for receiving non-electric signals and/or has a pressure pulse generator and/or a beater preferably with electroactive polymers, and/or an ultrasound transmitter and/or an infrasound transmitter. A design with electroactive polymers is only one possibility of designing the beater. A piezoelectric beater or a magnetic beater or a magnetorestrictive beater or another beater could also be used.

Alternatively or additionally, the communication device can be configured for detecting data with respect to at least one parameter of the total fluidic system and/or of a parameter of a fluid conducted in the total fluidic system, in particular in the line fluidically connecting the devices to one another.

In this case, the communication device comprises a corresponding sensor system for detecting data with respect to the at least one parameter, wherein the parameter preferably reflects the conductivity, temperature, the flow volume, the optical permeability, transmissivity, the absorption behavior, the cloudiness, the turbidity, or the transparency of the fluid and the parameter of the total fluidic system, for example, reflects an operating state or a maintenance state. The parameter can furthermore also reflect the density of the fluid or the concentration of individual ions in the fluid.

Alternatively or additionally, the communication device can also have a reception unit that can receive or read data from a different instance/device, in particular data with respect to the at least one parameter. It would equally be conceivable that the communication device only has one such reception unit, but is not itself configured to detect data with respect to the at least one parameter.

The communication device can be portable or stationary.

The communication device can be configured for online or offline operation. Online operation is to be understood here such that the communication device is coupled into the ongoing operation of the fluidically connected devices or of the total fluidic system and, for example, detects data with respect to a parameter of a fluid conducted in the lines fluidically connecting the device. Online operation is furthermore to be understood such that the communication device is connected to further data processing devices so that the communication device can, for example, always be controlled or can exchange data. In offline operation, the communication device is separated from the ongoing operation of the fluidically connected devices or of the total fluidic system and, for example, transmits analysis results that were prepared on the basis of the data with respect to the parameter of the fluid. Where required, the communication device can be coupled into the ongoing operation of the fluidically connected devices or of the total fluidic system. Offline operation is furthermore to be understood such that the communication device works autonomously or is not in communication with further data processing devices so that the communication device cannot be accessed by further data processing devices in this operating mode.

The communication device can be configured to detect, receive, and/or to transmit data continuously or intermittently.

Communication devices in accordance with the invention can, for example, be arranged at one or more positions in a fluidic system having a plurality of devices fluidically connected to one another and can thus, for example monitor the operation of the system and forward the detected data to a central processing station or also process them in a decentralized manner in the respective communication devices.

Communication devices in accordance with the invention can, however, also be used as part of a kit for the diagnosis of a fluidic system. Such a kit comprises at least one communication device in accordance with the invention, preferably a plurality of communication devices, that a user/service engineer can, for example, arrange at a line of the fluidic system for the diagnosis of a fluidic system, whereupon the at least one communication device detects data and provides them for a diagnosis of the maintenance/operating state of the system.

The at least one communication device in accordance with the invention of the diagnosis kit of a water preparation system can, for example, in particular detect signals output by a reverse osmosis system or by at least one apparatus such as a blood treatment machine. Error sources within the system can be localized and directly eliminated by a positioning of the at least one communication device in accordance with the invention of the diagnosis kit at different positions within a total fluidic system.

Signals can, for example, be output by a water preparation system such as a system for the provision of dialysis water, over an associated water line, said signals reflecting a parameter of the provided dialysis water. This parameter can for example, be the conductivity, the pressure in the fluidic system, a volume flow rate, or a turbidity. The at least one communication device in accordance with the invention of the diagnosis kit can be arranged, for example, at a specific position along the water line and can there receive the signals output by the water preparation plant. These signals can, for example indicate a desired value/reference value that can be compared with a measured value of the same parameter locally determined by the communication device. The communication device can thus e.g. determine the conductivity of the dialysis water at a specific, but arbitrary position in the total fluidic system as an actual value and a comparison can thus be made between the desired value and the actual value. If the communication device is positioned at different positions in the total fluidic system, any error source (for example a contamination that changes the conductivity) can be localized in the total fluidic system. Alternatively or additionally, a plurality of communication devices can preferably be used simultaneously at different points of the total fluidic system to localize any error sources.

A further aspect of the present invention relates to a method of non-electric communication between devices that are fluidically connected to one another, with the non-electric communication taking place over at least one line fluidically connecting the devices, preferably by means of pressure signals and/or acoustic signals.

At least one communication device in accordance with the invention is preferably arranged at at least one position in a total fluidic system formed by the devices that are fluidically connected to one another, said communication device preferably being configured for detecting data and/or for receiving non-electric signals and/or transmitting non-electric signals.

The non-electric communication preferably takes place via a liquid conducted in the line fluidically connecting the devices or via a gas conducted in the line fluidically connecting the devices.

It has furthermore proved to be advantageous if the at least one communication device in accordance with the invention is configured for detecting data, with the data detected by the at least one communication device reflecting at least one parameter of the total fluidic system and/or a parameter of a fluid conducted in the total fluidic system, in particular in the line fluidically connecting the devices to one another.

The method in accordance with the invention is preferably applied to a total fluidic system that has at least one water preparation system and/or at least one treatment machine, in particular a blood treatment machine, and/or at least one line, in particular a supply line, a loop, a water line, a dialysis line, or a concentrate line.

A plurality of communication devices in accordance with the invention are preferably used as part of a method in accordance with the invention that are arranged at different positions of the total fluidic system.

Another aspect of the present invention relates to a system for the non-electric communication between devices that are fluidically connected to one another, characterized by at least one communication device in accordance with the invention that is arranged at at least one position of the total fluidic system and is configured to communicate non-electrically, preferably by means of pressure signals and/or acoustic signals, over at least one line fluidically connecting the devices to one another, preferably a fluid conducted in the line.

The system preferably has at least one water preparation system and/or a concentrate supply system and/or at least one treatment machine, in particular a blood treatment machine, and/or at least one line, in particular a supply line, a loop, a water line, a dialysis line, or a concentrate line that are fluidically connected to one another and thus preferably form a total fluidic system. The water preparation system is preferably a system for providing prepared water for the dialysis. The water line preferably serves the conducting of prepared water for the dialysis; the concentrate line preferably serves the conducting of concentrate for the dialysis.

The fluid used as part of the invention is preferably prepared water for the dialysis or dialysis water. Prepared water for the dialysis or dialysis water is to be understood here as water that satisfies the requirements of the standard ISO 23500 and is thus provided for use in dialysis. The invention can, however, also furthermore be applied to pure water, ultrapure water, or ultrapurified water. An example for pure water is drinking water. Ultrapure water is characterized by a higher degree of purity than pure water and ultrapurified water is even purer than dialysis water.

The present invention can be used for the communication of the most varied devices that are fluidically connected to one another. Active and/or passive devices in corresponding devices such as water preparation systems, medical devices (blood treatment device, dialysis machine, etc.) can be fixedly or releasably arranged here. The communication devices can also be designed as portable and can, for example, be arranged for the purpose of diagnosis/functional monitoring at a device or at the total system fluidically connecting the device. Some communication forms/communication parameters will be named by way of example in the following on which the invention can be used.

Communication can take place between a first and a second reverse osmosis system by means of a communication method in accordance with the invention and/or at least one or also a plurality of communication devices in accordance with the invention.

Communication is equally conceivable between a reverse osmosis system and at least one communication device for the purpose of diagnosis/functional monitoring, e.g. of the reverse osmosis system. In a similar manner to this, a medical device can also communicate with at least one communication device for the purpose of diagnosis/functional monitoring.

The present invention can furthermore be used for communication between a reverse osmosis system and a medical device (blood treatment device, dialysis machine, etc.) or for communication between at least two medical devices.

A further application case relates to the communication between a medical device and a local water preparation apparatus. The local water preparation apparatus can, for example, be an adsorber or a similar apparatus for refreshing used dialyzate in situ. The used dialyzate can, for example, be led past the adsorber and can be reused so that a closed recycling circuit is formed. The medical device and the local water preparation apparatus can here be arranged in a common housing and/or can be fixedly installed with one another.

Another application case relates to the communication between a medical device and a local water preparation apparatus. The local water preparation apparatus here provides the amount ("batch") of dialysis fluid locally required for the treatment before the treatment that is mixed from dialysis water and concentrate. The medical device and the local water preparation apparatus can here be arranged in a common housing and/or can be fixedly installed with one another.

In the aforesaid examples, a flash distillation system can also be used instead of the reverse osmosis system for the preparation of ultrapure water/pure water. The medical device and the flash distillation system can here also be arranged in a common housing and/or can be fixedly installed with one another. The reverse osmosis system and the flash distillation system are examples for a water preparation system.

The present invention can furthermore also be used for any desired combinations of the aforesaid communication partners.

The key idea of the present invention can be expressed as follows in other words It is sensible in water technology of medical devices such as dialysis stations to know and to monitor the state of the installation/the technology.

Networked water technology installations are frequently used for this purpose that provide the user with data such as the temperature, conductivity, yield, etc. of a water preparation system such as a reverse osmosis (RO) system.

The disadvantage of this conventional solution is that only data are recorded and thus provided that were directly detected or were directed in the direct environment of the water preparation system or of the reverse osmosis (RO) system.

In accordance with an aspect of the present invention, provision is therefore made to, for example, provide distributed communication devices in the periphery of a fluid line such as a loop that collect, evaluate, and forward data locally at different points in the fluid line system.

In this respect, the communication devices can be equipped with actuators with whose aid the communication devices can introduce signals into the fluid line, e.g. loop/concentrate line. The communication devices can thus act as active transmitters.

The state of a system (water preparation system) in which the fluid line is fluidically coupled and errors and failures can thereby be recognized, for example, and, if multiple communication devices are provided, can also be locally assigned/localized. In principle, only one communication device can also be provided in the system (water preparation system) in which the fluid line is fluidically coupled.

In more complex systems, for example water preparation systems in hospitals or dialysis centers, it may be sensible to provide a plurality of communication devices. One communication device per floor can be provided, for example; a local detection of an error on a floor then results in the shutting down of the respective floor while the operation on the other floors can be continued without change.

The communication devices can be networked with one another. This has the advantage that in addition to errors, for example, operational routines such as chemical or hot disinfection can also be optimized and adapted to the respective environmental conditions since communication devices detect the conditions at different positions in the fluid system and thus permit an uninterrupted and comprehensive monitoring of the system.

In accordance with an aspect of the invention, communication devices are distributed at the fluid line or loop/concentrate line that preferably comprise sensors for detecting data and/or actuators for transmitting signals. Information from the periphery can thereby be used for evaluating the state of the total water preparation system and of any medical devices connected thereto and for optimization in the operating routine.

An application of the present invention thus comprises the prediction of required maintenance work ("predictive maintenance"), whereby a smooth function of a water preparation system can be ensured.

Expressed in other words, the present invention can also be described as follows:

There is conventionally no possibility of checking the sensors (temperature, pressure, conductivity, etc.). present in medical devices or treatment machines connected to a central water supply at the installation site of the treatment machines (in situ) for their correct functional capability.

It is thus an object of the present invention to provide a simple possibility for on site checking of the sensors of medical devices or treatment machines connected to a central water supply.

A communication device in accordance with the invention in a simple embodiment has a receiver that receives signals transmitted over the water line from the central water supply (or from a transmitter connected thereto) and forwards them to a circuit that can display the signals to an operator and/or can make them accessible to a treatment machine.

The signals can describe properties of the water provided by the central water supply, for example a conductivity that is measured at the outlet of the water supply (and that is a measure for the purity of the water), a pressure in the system, a temperature, a (volume) flow, etc.

A display can be provided to display the received signals that preferably serve as a reference and/or an interface can be provided that forwards the signals to a device having a display (wired/wireless).

The treatment machine can additionally make the signals accessible via a wireless or wired interface where they are either displayed on a display of the treatment machine or are internally compared with corresponding values of the sensors present in the machine, e.g. as part of a running test program, whereby the function of the sensor is checked.

The communication between the central water supply (or the transmitter connected thereto) and the communication device takes place, for example, via pressure pulses, dynamically modified conductivity values, or similar signals that can be forwarded by the fluid in the lines.

On an arrangement in which a plurality of treatment machines are connected to a common loop, it may be necessary for the measurement of the parameters of the treatment machines or of the line system that only one machine is always operable at any one time. This can be ensured, for example, by a corresponding communication and control of the machines among one another or, if a communication device is provided at or connected to each of the machines connected to the same loop that can activate the respective treatment device via an interface by a selection starting from the central water supply and by activating the respective treatment device to be checked.

There is a further possibility to provide a controllable valve in the communication device by means of which the water supply is only opened/switched for the treatment device respectively selected for inspection while the other treatment devices are cut off from the water supply by the valves of the communication devices associated therewith. The communication device in this embodiment has a unique address via which it can be individually addressed.

If the central water supply does not provide any measured values on properties of the water, a communication device equipped with corresponding sensors can be connected into the water circuit. This can take place at a central point or at individual loops of a larger system having a plurality of loops.

Expressed in other words, the present invention can also be described as follows:

A key element of the present invention is the fact that different devices of a fluidically connected system are physically connected to one another via at least one fluid line (for example for dialysis water, ultrapure water, pure water, ultrapurified water, and/or dialysis concentrate, and/or dialyzate, and non-electric communication takes place between the devices over this fluid line.

This non-electric communication can, for example, take place using signals in the form of pressure pulses and/or acoustic waves. The sound frequency ranges are preferably outside the audible range (ultrasound and infrasound).

For example, communication devices in accordance with the invention can be used within the framework of a central water technology system or concentrate system. In this configuration, the water preparation system is a (central) water technology system (e.g. reverse osmosis [RO] system or distillation system or flash distillation system) for providing ultrapure water (e.g. for dialysis) or a concentrate provision system that e.g. provides dialysis concentrate.

The system has communication devices or means for communication over the water line/concentrate line (that enable at least a transmission of signals) such as means for generating pressure pulses in the water line or for transmitting acoustic signals.

The system furthermore has a loop that conducts ultrapure water from the water technology system to the removal points (points of use) or a concentrate line that leads from a concentrate provision system to points of use.

At least one communication device is furthermore provided that is (preferably releasably) attached to the loop or to the concentrate line and has means for receiving the signals of the system, e.g. a microphone or a pressure measuring means or an ultrasound receiver.

The communication device preferably has means for evaluating the received signals. The communication device furthermore has means for displaying the evaluated signals and/or means for a wired or wireless transmission of the evaluated signals to a further instance (local, remote, control center, server, display tablet for maintenance, treatment device).

In advantageous further developments, the at least one communication device also has means for transmitting a signal.

In accordance with another aspect of the invention, portable communication devices can be used that act in isolation.

Three alternative examples are conceivable here:

In the first example, two communication devices are provided that, instead of treatment units, are connected to two different points at a fixedly installed liquid line and have a sensor system for detecting data with respect to the conductivity of the water, the volume flows, etc.

These two communication devices can measure properties of the fluid system or of the water system (water preparation system and associated lines) and communicate with one another over the (water) line. A triangulation of an error that results in characteristic sound emissions (fluttering, defective valve; flow noise/whistling) due to a line constriction) is thereby possible, for example. The monitoring of the line system can therefore be improved.

In accordance with the first alternative, a central system, that provides the pure water and/or concentrate, is equipped with means for transmitting signals of non-electric communication but the local lines are not necessarily equipped with devices for reception in standard everyday operation.

In the diagnostic case/service case/on the putting into operation, a mobile communication device can be attached to a fluid line to receive non-electric signals and to thus contribute in a supporting manner to diagnosis/to service/to putting into operation or to additionally also transmit signals e.g. with respect to the measured data.

In accordance with a second alternative, the two (or more) communication devices serve to enable non-electric communication between medical devices/treatment machines. At least one communication device has to have a transmitter for this purpose and the other(s) have to have at least one respective receiver.

If a simultaneous operation of a plurality of treatment machines (e.g. in specific operating modes) is unwanted or not permitted, a coordination of the treatment machines with one another can take place in this manner The treatment machines are for this purpose connected to the communication devices, for example via a so-called "legacy interface" or the like.

The present invention can furthermore be expanded to treatment machines and to the associated infrastructure.

In this configuration, a treatment machine is part of the system enabled for non-electric communication in accordance with the invention or vice versa. Accordingly, a treatment machine (e.g. a hemodialysis unit) also has means for receiving and/or for transmitting non-electric communication signals over a fluid line.

The advantages of the present invention comprise, expressed in summary, an electrical connection of the devices forming the system being able to be avoided and an anyway present line also being used in addition to the exchange of fluid media for the exchange of non-electric signals. In other words, communication between devices is made possible even though they are not electrically connected to one another. The risk is thus also eliminated that electric shocks or other electric interference can escalate in the system. Such a risk would accompany an electric coupling.

Again expressed in other words, the present invention thus comprises the base ideal of using one or more existing fluid lines and in particular fluid-conducting lines for preferably active communication of devices connected by means of these fluid line(s).

Different hardware designs in accordance with the invention will be explained in the following.

A simple embodiment of the invention comprises at least one passive communication device that only acts offline and logs data that it then forwards (also wirelessly) over a communication line e.g. to the water preparation system.

Such a communication device is equipped with a receiver that is, for example, a microphone or an ultrasound receiver (piezo element). The communication device monitors the function of the total system and thus detects data with respect to maintenance states such as storage damage to parts, fluttering of valves, and the power/speed pump for consumption optimization/control An evaluation of the signals communicated by the communication device takes place in the water preparation system/RO system and thus in a centralized or central manner in the target system. In this variant, the communication device acts as a passive receiver having a data line for forwarding signals. In principle, a further communication device could also be provided that is configured to transmit signals through the fluid lines of the system.

Operating modes and maintenance states can thus be recognized and e.g. be displayed via a corresponding output of the communication device or of the water preparation system (e.g. optical signals such as colored lamps or also acoustic signals).

Alternatively or additionally, the at least one communication device can also be equipped with an integrated unit for data processing. The data detected by means of the receiver (e.g. microphone or ultrasound receiver (piezo element)) are processed directly in the communication device in this variant and for this purpose the communication device is equipped with the corresponding hardware, µC and RAM and software.

The communication device in this variant has a communication line (also wireless) to any other desired further instance and operating modes/maintenance states of the fluidic system can thus be recognized and e.g. displayed via a corresponding output of the communication device (e.g. optical signals such as colored lamps or also acoustic signals) and/or the further instance and/or the water preparation systems.

This variant furthermore provides the advantage that even if no data lines are installed within a dialysis center, for example, for electric data communication, commands can be exchanged between a plurality of medical devices of a plurality of medical devices, with the communication device in accordance with the invention serving as a translator of the commands or of a specific command into a data/status/or control signal The communication device is also offline in this example. No designated communication lines thus have to be provided, but the already existing fluid lines can also be used for the communication.

Existing medical devices and/or water preparation systems and/or fluidic systems can be retrofitted with at least one communication device in accordance with the invention that provides the advantage that information can be actively exchanged via a defined interface (protocol, I/O digital, analog). The following communication interfaces/protocols can inter alia be used RS232, RS422/485, CAN Bus, CANopen, PROFIBUS, PROFINET-RT, Ethernet/IP, Modbus, OPC, Bluetooth, WiFi, SCSI, IDE, ATA, SATA, Firewire, USB, PCI, PCI-E, AGP, GPIP, Rocket link, Thunderbolt, VGA, DVI, HDMI, GSM, UMTS/3G, LTE/4G, 5G, Ethercat, telecontrol protocol in accordance with IEC 60870-5-10x, and—in particular for retrofitting—engineer and production accesses such as SPI, I2C, LIN.

A further embodiment variant in accordance with the invention provides at least one passive communication device that is online and that can be accessed from external or that can be controlled from external.

In accordance with this embodiment, the at least one communication device comprises a receiver, for example in the form of a microphone or ultrasound receiver (piezo element).

The at least one communication device furthermore has a communication line (also wireless) to a gateway that transmits data into a cloud for processing and evaluation and returns feedback to the water preparation system or RO system, to medical devices/machines connected to the water preparation system, or to the at least one communication device.

Existing medical devices and/or water preparation systems and/or fluidic systems can be retrofitted with at least one communication device in accordance with the invention that provides the advantage that information can be actively exchanged via a defined interface (protocol, I/O digital, analog).

This variant furthermore also provides the advantage that even if no data lines are present, for example within a dialysis center, commands can be exchanged between a plurality of medical devices of a plurality of medical devices, with the communication device in accordance with the invention serving as a translator of the commands or of a specific command into a data/status/or control signal. The at least one communication device is online in this example.

The above-described passive communication devices can be used in the semiautomatic putting-into-operation mode of at least one medical device and/or of a water preparation system.

A plurality of portable or stationary communication devices are preferably used here that, for example, enable a triangulation for detecting an exact position of a medical device.

Such a design furthermore also allows an efficient error monitoring and diagnosis if, for example, the locally recorded data from different communication devices in a fluidically connected total system having at least one medical device and/or at least one water preparation system are compared with one another.

It has proved advantageous with such a system having a plurality of communication devices and/or a plurality of medical devices and/or a plurality of lines/water preparation systems if the different components (communication devices and/or medical devices and/or lines/water preparation systems) each have individual IDs and are thus individually addressable.

In accordance with a further aspect of the invention, at least one active communication device can be provided that is either online or offline. Such an active communication device comprises means for transmitting signals of non-electric communication, e.g. a pressure pulse generator, a beater with electroactive polymers, an ultrasound transmitter, an infrasound sensor, or similar.

The data and/or control data for generating signals to be transmitted or also other date detected by means of a sensor or receiver (e.g. microphone or ultrasound receiver (piezo element)) are processed directly in the communication device in this variant and for this purpose the communication device is equipped with the corresponding hardware μC and RAM and software.

The communication device in this variant has a communication line (also wireless) to any other desired further instance such as the water preparation system/RO system and operating modes/maintenance states of the fluidic system can e.g. be displayed via a corresponding output of the communication device (e.g. optical signals such as colored lamps or also acoustic signals) and/or the further instance and/or the water preparation system.

In accordance with another aspect of the present invention, communication devices in accordance with the invention are provided, for example, at a line of the fluid system or at different fluidically connected lines or at different points.

Every communication device comprises a sensor that, for example, detects the volume flow, the conductivity, the transparency, the temperature, or another parameter of a fluid flowing in the line. Each communication device is additionally configured to forward the detected data on the same fluid to at least one other communication device and/or to the water preparation system and/or to any other further instance. The non-electric signal transmission takes place, for example, by means of a pressure pulse generator, of a beater with electroactive polymers, and/or of an ultrasound transmitter or of an infrasound transmitter.

In other words, the measurement medium (that is a fluid such as dialysis concentrate or pure water, that is the subject of a detection/measurement of parameters, e.g. temperature) simultaneously serves as a communication medium in accordance with the invention. Due to the distributed arrangement of the communication devices and thus sensors, information is logged in a targeted manner and locally at critical points of the total system, e.g. at a point of use. For example, in hot disinfection, the temperature of the fluid, and in thermal disinfection, the conductivity of the fluid, Is detected at a plurality of points of the total fluidic system.

This enables a particularly good optimization of the control processes and of the system modes with respect, for example, to the used temperatures, energy. flushing cycles, and/or flushing amounts, etc. As described above, the data processing can take place either in a decentralized manner in every communication device or in a centralized manner. Control and communication can thereby take place e.g. advantageously in a system having a plurality of medical devices that require regular disinfection—e.g. with hot water—such that not all the medical devices are simultaneously disinfected so that the demand on the power of the disinfection process or on the disinfectant can be reduced. A part of the machine can thus, for example, respectively be sequentially disinfected because then only a smaller amount of disinfectant, e.g. hot water, has to be provided at a specific time. In the case of hot water, a tank could then be reduced in size or the heating power of a heating device could be reduced.

The individual communication devices can first also additionally forward the detected data over a communication line (also wirelessly) and operating modes/maintenance states of the fluidic system can e.g. be displayed via a corresponding output of the communication device (e.g. optical signals such as colored lamps or also acoustic signals) and/or the further instance and/or the water preparation system.

The data detected by the communication devices can be compared with one another and/or with otherwise stored reference values to determine the operating modes/maintenance states.

Provision is made in accordance with another aspect of the invention to use at least two communication devices in accordance with the invention in accordance with one of the above variants as part of the functional monitoring of a medical device such as a blood treatment machine.

The at least two communication devices in accordance with the invention can, for example, be used at an infeed and an outfeed line of the medical device or at two other points in the fluidics of the medical device. In the case of a blood treatment machine, the at least two communication devices in accordance with the invention can each be arranged in a line of the RO system and in a concentrate line.

The function of the water technology of the medical device can be monitored and evaluated by means of the at least two communication devices in accordance with the invention. A conclusion can furthermore be drawn on a respective operating mode of the medical device. A plausibility check of the data detected by the at least two communication devices in accordance with the invention can furthermore take place for recognizing error cases.

For example, a parameter of the fluid can be measured at an inflow and outflow line of the medical device, e.g. a dialysis machine, each having a communication device, and a conclusion can be drawn on the function of the medical device from a comparison of the measured values with one another. For example, the turbidity of fresh dialysis fluid can be measured by means of a first communication device before the introduction into the dialyzer. In addition, the turbidity of used dialysis fluid can be measured by means of a second communication device downstream of the dialyzer An increased turbidity of the used dialysis fluid relative to the fresh dialysis fluid can, for example, indicate a leak in the dialyzer and thus traces of blood in the used dialysis fluid.

Alternatively or additionally, a central control unit, a water preparation system, or the medical device or the dialysis machine can, however, also output signals relating to a desired temperature of the dialysis water or of the dialysis fluid by means of the non-electric communication in accordance with the invention. Communication devices arranged at different positions of the fluidic total system, e.g. at the dialysis machine, can thereupon locally detect the temperature of the dialysis water or of the dialysis fluid and can transmit the corresponding measured values to the dialysis machine, and/or locally evaluate them, and/or forward them to a central control unit, a further analysis device, or a display unit. Dialysis fluid is here to be understood as dialysis water with added concentrate that contains the components required for the treatment. in an appropriate amount.

If, for example, the medical device is a blood treatment machine (dialysis machine) and if a communication device in accordance with the invention detects that no dialysis water or permeate is used, while the other communication device detects that concentrate is used, this indicates an error case and in particular a leak. If, in contrast, it is detected by the communication device that dialysis water or permeate is used and if it is detected by the other communication device that concentrate is simultaneously used, this indicates that the dialysis machine is operated for carrying out a treatment and thus for providing dialysis fluid. The data detected by the communication devices can thus be compared with one another and/or with otherwise stored reference values to determine the error cases/operating modes (maintenance states.

A further aspect of the invention relates to the retrofitting of component units, in particular water preparation systems and medical devices, with communication devices in accordance with the invention by means of which information can be advantageously actively exchanged over defined interfaces (protocol, I/O digital, analog, etc. and the further aforesaid interfaces).

For example, the present invention can also serve as measurement equipment for service engineers for a fast diagnosis/technical safety control of lines, in particular loops (leaks) or of the medical devices and/or water preparation systems connected thereto.

Communication devices in accordance with the invention can advantageously be used asl local evaluation units similar to service software. At least one communication device in accordance with the invention is used as a diagnostic unit in this case. A diagnosis kit having a plurality of communication devices in accordance with the invention can also be provided.

For example, a service engineer brings along one (or more) portable communication devices in accordance with the invention into a treatment center/dialysis center (that does not have to be equipped with communication devices in accordance with the invention) and arranges the communication device in accordance with the invention e.g. at a point of use in a treatment room at a loop of a water preparation system where otherwise a medical device/treatment machine would be connected.

A diagnosis of the loop can already be carried out using a communication device in accordance with the invention connected in this manner. Alternatively or additionally, the service engineer could compare a value measured at/by, the communication device in accordance with the invention with the measured value of the same parameter of an adjacently connected treatment machine to thus be able to draw conclusions on operating modes, operating states, maintenance states, and error cases.

In further developments of the invention, there are further instances that the engineer includes in the diagnosis such as a transmitting RO system and/or a further communication device in accordance with the invention, as has been described above.

In this embodiment of the invention, a parameterization/setting can take place at the distributed communication devices in accordance with the invention. The use of a plurality of communication devices in accordance with the invention for the system diagnosis enables a fast overview of the total structure of the treatment center and of the infrastructure or type of the devices and operating states.

The state of individual medical devices can be polled by means of the at least one communication device for central maintenance measures (e.g. disinfection of the RO system). Specific operating modes can thereupon be directly prohibited, e.g. individual devices can be switched on or switched off/controlled from e.g. to interrupt an ongoing treatment or to flush, and data can be polled.

Since all this is determined by means of the at least one communication device or the plurality of communication devices, the walking distances are reduced for the service engineer. A direct switching of devices into specific service modes or for a maximum capacity of the parameterization of central systems (RO, concentrate) can thereupon take place.

It has furthermore proved advantageous if communication devices in accordance with the invention are portable/mobile/carriable. Alternatively, they can also be designed as stationary, however.

Portable communication devices can additionally preferably be connected to a water preparation system, in particular to an RO system, such as a medical device or a treatment machine. Communication devices in accordance with the invention can additionally be passive or active and can be configured for online or offline operation.

In accordance with a further aspect of the invention, the invention is used on a system having an RO system, a treatment machine, and other infrastructure machines (such as air conditioning plants, heating systems, water treatment systems, etc.).

In accordance with an embodiment of the invention, the treatment device comprises components of an active communication device in accordance with the invention. In other words, the function of the communication device in accordance with the invention is integrated in the treatment machine.

The active communication device is either online or offline, as described above.

Such an active communication device comprises means for transmitting signals of non-electric communication, e.g. a pressure pulse generator, a beater with electroactive polymers, an ultrasound transmitter, an infrasound transmitter, or similar. The data and/or control data of a receiver (e.g. a microphone or ultrasound receiver (piezo element)) for generating signals to be transmitted or also other data are preferably directly processed in the communication device in this variant and for this purpose the communication device is equipped with the corresponding hardware μC and RAM and software.

The communication device in this variant has a communication line (also wireless) to any other desired further instance such as the water preparation system/RO system and operating modes/maintenance states of the fluidic system can thus e.g. be displayed via a corresponding output of the communication device (e.g. optical signals such as colored lamps or also acoustic signals) and/or the further instance and/or the water preparation system.

The treatment machine can have additional sensors for detecting the conductivity of a fluid, the temperature, density, the flow volume, etc. Additional information with respect, for example, to a disinfection process, to hygiene, or also to media properties is delivered in this manner. For example, the treatment machine can deliver measured values on a hot disinfection with respect to the temperatures present in the internal fluidics of the treatment machine or can deliver measured values in a chemical disinfection with respect to the conductivity of the fluid flowing in the internal fluidics of the treatment machine. If a plurality of treatment machines are provided, for example in a dialysis center, every treatment machine can transmit the corresponding measured values to a central control. The settings/conditions in each treatment machine can then be individually optimized on the basis of the transmitted values, for example by a targeted local adaptation of the temperature or by a targeted local metering pf disinfectant.

This embodiment thus provides the advantage that a central measurement of the parameters can also take place so that such a control/regulation can be carried out so that optimum conditions are always reached at a defined point of use. In addition, a coordination and/or evaluation of all the demands of different consumers can take place.

Alternatively or additionally, in accordance with another aspect of the invention, provision can also be made with such a system that a passive communication device in accordance with the invention is used in combination with an actively transmitting treatment machine as part of a fluid system.

In this case, the treatment machine comprises means for transmitting signals of non-electric communication, e.g. a pressure pulse generator, a beater with electroactive polymers, an ultrasound transmitter, an infrasound sensor, or similar. The passive communication device detects, as described above, the signals of the treatment machine by means of a receiver (e.g. a microphone or ultrasound receiver (piezo element)).

This embodiment provides the advantage that processes and in particular the consumption control (energy, water, disinfectant, etc.) can be optimized. The invention in accordance with this embodiment can thus preferably be implemented as part of a fluid on demand system.

In such a variant, both the communication device in accordance with the invention and the treatment machine are active and thus transmit non-electric signals. The treatment machine and/or the communication device here each have a receiver (e.g. a microphone or ultrasound receiver (piezo element)) and/or means for transmitting signals (e.g. a pressure pulse generator, a beater with electroactive polymers, an ultrasound transmitter, an infrasound sensor, or similar).

The RO system could, for example, communicate a conductance value to the fluidically connected treatment machines in the form of pressure pulses (one pulse per microsiemens). A problem could arise here if the treatment machine has a water inlet chamber that makes a transfer of sound and pressure pulses from the ring unusable for communication purposes.

It would be conceivable to arrange at least one communication device in accordance with the invention close to at least one treatment machine that receives the pulses from the RO system and forwards them to the treatment machine. It would be conceivable, alternatively thereto, that the treatment machine has a microphone (e.g. for structure-borne sound) at the loop so that an efficient communication can take place between the RO system and the treatment machine despite any water inlet chamber of the treatment machine since the water inlet chamber cannot represent any problem for the sound recording.

In summary, it must be stated that the present invention provides the following advantages:

Non-electric communication takes place via a fluid or a liquid in a line such as a dialysis water line. This is in particular very advantageous in the medical sector since electric communication is in particular suboptimal and thus to be avoided in the context of fluid conducting lines or water preparation systems.

Communication is furthermore possible over the dialysis concentrate line (and not only over lines of the water preparation system (water treatment)), for example, on a use of the invention on a blood treatment machine or on a dialysis machine. A possible second communication path between the components of the fluid system is thus produced by the integration of the concentrate and a concentrate loop.

A further advantage of the invention comprises very protected communication since the fluid lines and thus in accordance with the invention the communication paths of medical fluid conducting systems do not have any connection to the outside world since, for example, the water supply is decoupled/separated from the outside world by a free inflow (EN 1717).

There is furthermore the possibility of providing an additional interface for the encrypted transmission using other means (wireless LAN, a sequence of QR codes following one another in time (OR stream), electric) in addition to the non-electric communication.

The present invention thus enables an active coupling/transport of information in the fluid/liquid conducted in a line. This information relates, for example, to the removal, removal amount, the operating state, the request for medium, an information standby, status information of the connected units (unidirectional and bidirectional), start/stop communication, the detection of concentrate types for the concentrate selection, etc. Queries can thus be answered, such as whether the concentrate selected at the HD unit is in the loop.

In the method in accordance with the invention or in the apparatus, a safety function for blocking/releasing specific operating modes can furthermore be implemented in dependence on the medium or operating phase (disinfection/supply, etc.).

The present invention enables an efficient monitoring of changes to the installation/units.

In addition, the present invention makes it possible to check which medium is in a line (disinfectant, dialysis concentrate, water, dialysis water, hot water) and thus to recognize and to ensure a specific operating state (e.g. disinfection, supply) of a medical device or of a water preparation system.

The present invention additionally enables a temperature monitoring of the medium/fluid in a line or a loop. The temperature of the medium, for example, influences its density (known loop constellation) and a corresponding signal is output by a communication device in accordance with the invention as part of a temperature monitoring.

The present invention furthermore enables a simple measurement of a line, e.g. of a loop, at which a plurality of treatment machines are arranged for the characterization for installation and service purposes and for the optimization of the operation. Optimum flushing amounts, disinfectant amounts, hot water amounts, ventilation cycles, etc. can thus be set, for example, while the function of the total fluidic system is monitored locally and directly by the communication devices in accordance with the invention. The fluidic system can also be optimized with respect to the number of connections and with respect to the location/the position of removal points. The present invention can furthermore be used for recognizing contaminants (e.g. air bubbles, bacterial growth, etc. in lines/the loops.

In addition to this, the present invention provides a good possibility for leak recognition, leak tightness test during the installation and in the operating phase of the fluidic system.

Further advantages, features, and effects of the present invention result from the following description with reference to the Figures. The same reference numerals in the Figures designate the same or similar components. There are shown:

FIG. 1 the general structure of a fluid supply for a plurality of blood treatment machines by means of a loop such as is frequently used in dialysis centers;

FIG. 2 the structure of FIG. 1 with communication devices arranged along the loop;

Figure 1:
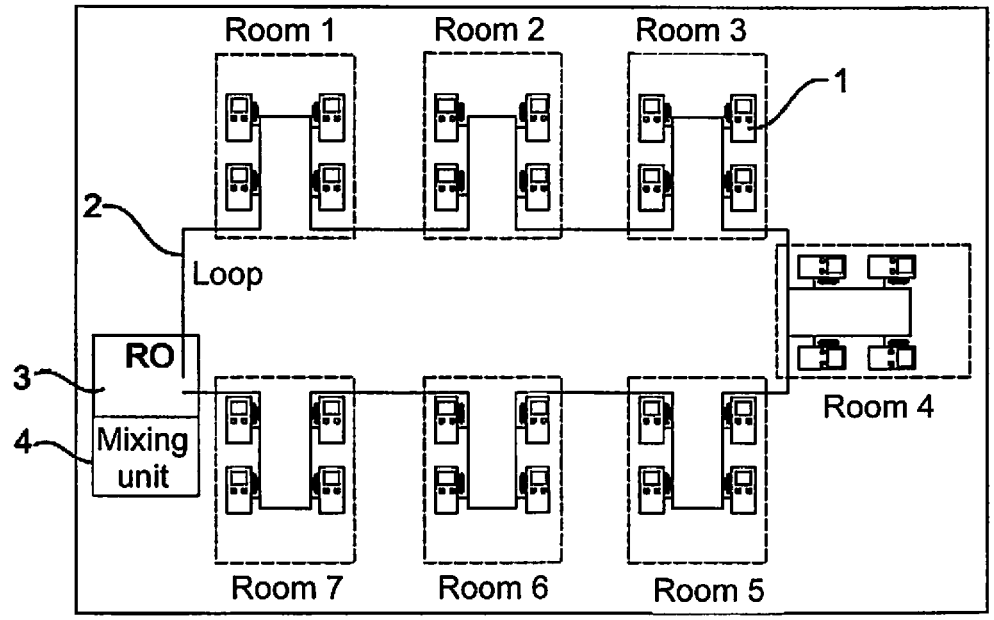

FIG. 1 shows a plurality of blood treatment apparatus 1 that stand in a plurality of different rooms and are fluidically connected to one another via a loop 2 and to a water preparation system/RO system 3 and to a mixing unit 4 for generating dialysis solution from concentrate and thus form a total fluidic system.

Figure 2:
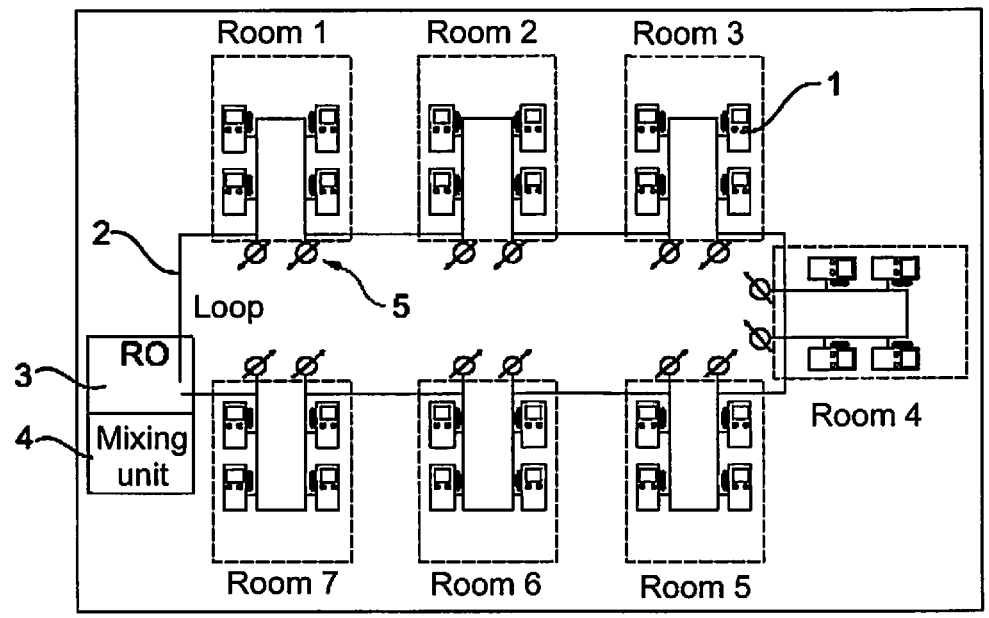

FIG. 2 shows the structure of FIG. 1 with communication devices 5 arranged along the loop 2. The communication devices 5 in this arrangement, for example, enable the detection of data/measurement of data with respect to the fluid/the liquid in the loop 2, for example the flow volume, the temperature, or the conductivity. The arrangement of the communication devices 5 thus makes possible the detection of data for individual groups of blood treatment apparatus 1 without the operation of the other blood treatment apparatus 1 being impaired hereby or the other devices having to be set into a specific operating mode that could, for example, impair a (central) measurement.

It is in particular sensible with such arrangements having a plurality of devices (treatment units, water preparation systems, etc.) and a plurality of communication devices if both the devices and the communication devices each have individual IDs and are thus individually addressable.

Figure 3:
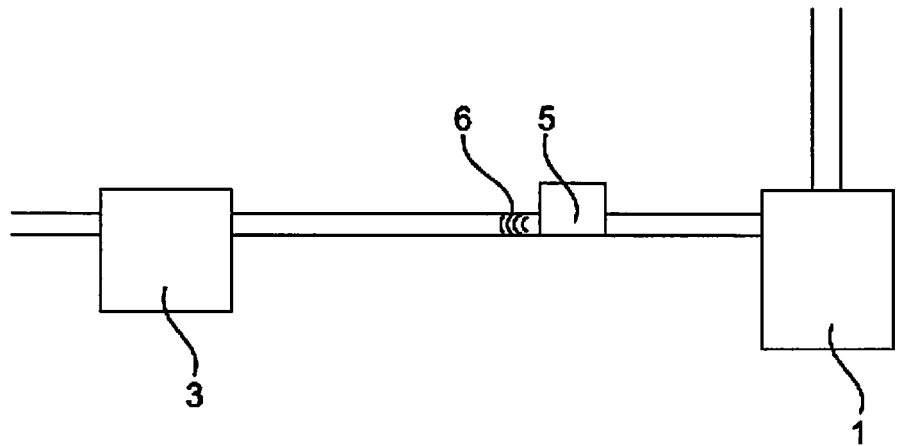
FIG. 3 shows a communication device in accordance with the invention that is arranged at a line between a blood treatment apparatus and a water preparation system or RO system 3 and transmits sound waves 6.

FIG. 3 shows a communication device 5 in accordance with the invention that is arranged at or in a line, for example a loop 2, between a blood treatment apparatus 1 and a water preparation system or RO system 3 and communicates acoustically by the transmission of acoustic signals into the fluid medium flowing in the line, as is illustrated by the sound waves 6.

Figure 4:
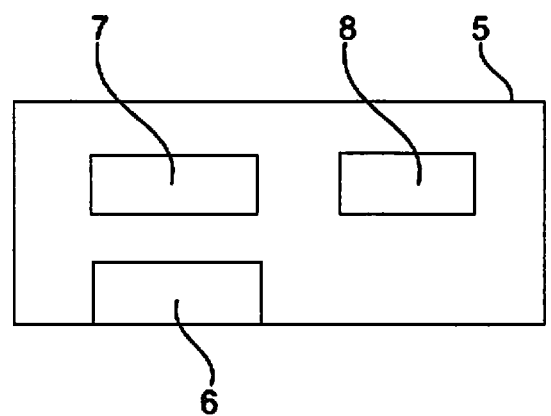
FIG. 4 shows the basic design of a communication device in accordance with the invention.

FIG. 4 shows the basic design of a communication device 5 in accordance with the invention. The communication device 5, for example, has a sensor/a sensor system 6 for detecting at least one parameter of the total fluidic system that is formed by the fluid lines and the apparatus coupled thereto.

The communication device 5 furthermore has a receiver 7 for receiving non-electric signals. The receiver 7 can e.g. be a microphone. In addition, the communication device 5 has a transmitter 8 for transmitting non-electric signals. The transmitter 8 can e.g. be a beater or an ultrasound transmitter.

The invention claimed is:

1. A communication device for non-electric communication between devices fluidically connected to one another, characterized in that the communication device is adapted to be arranged in a position in a total fluidic system formed by the devices fluidically connected to one another and to receive and/or transmit non-electric signals, in particular in the form of pressure signals or sound signals, with the non-electric signals being transmitted over a line fluidically connecting the devices to one another.

2. A communication device in accordance with claim 1, characterized in that the communication device has a microphone and/or an ultrasound receiver for receiving non-electric signals and/or has a pressure pulse generator and/or a beater, with electroactive polymers, and/or an ultrasound transmitter and/or an infrasound transmitter for transmitting non-electric signals.

3. A communication device in accordance with claim 1, characterized in that the communication device is furthermore configured for detecting data with respect to at least one parameter of the total fluidic system and/or of a parameter of a fluid conducted in the total fluidic system, in particular in the line fluidically connecting the devices to one another.

4. A communication device in accordance with claim 3, characterized in that the communication device has a sensor system for detecting data with respect to the at least one parameter, with the parameter preferably reflecting the conductivity, temperature, the flow volume, turbidity, or the transparency of the liquid, and the parameter of the total fluidic system, for example, reflecting an operating state or a maintenance state.

5. A communication device in accordance with claim 1, characterized in that, the communication device is portable or stationary.

6. A communication device in accordance with claim 1, characterized in that the communication device is configured for online or offline operation.

7. A kit for diagnosing a fluidic system comprising at least one communication device, preferably a plurality of communication devices, in accordance with claim 1.

8. A method of non-electric communication between devices that are fluidically connected to one another, characterized in that the non-electric communication preferably takes place over at least one line fluidically connecting the devices, preferably by means of pressure signals and/or acoustic signals.

9. A method in accordance with claim 8, characterized in that at least one communication device for non-electric communication between devices fluidically connected to one another is adapted to be arranged in a position in a total fluidic system formed by the devices fluidically connected to one another and to receive and/or transmit non-electric signals, in particular in the form of pressure signals or sound signals, with the non-electric signals being transmitted over a line fluidically connecting the devices to one another and is arranged in at least one position in a total fluidic system formed by the devices that are fluidically connected to one another, said communication device preferably being configured for detecting data and/or for receiving non-electric signals and/or transmitting non-electric signals.

10. A method in accordance with claim 8, characterized in that the non-electric communication takes place via liquid conducted in the line fluidically connecting the devices.

11. A method in accordance with claim 8, characterized in that the at least one communication device for non-electric communication between devices fluidically connected to one another is adapted to be arranged in a position in a total fluidic system formed by the devices fluidically connected to one another and to receive and/or transmit non-electric signals, in particular in the form of pressure signals or sound signals, with the non-electric signals being transmitted over a line fluidically connecting the devices to one another and is configured for detecting data, with the data detected by the at least one communication device reflecting at least one parameter of the total fluidic system and/or a parameter of a fluid conducted in the total fluidic system, in particular in the line fluidically connecting the devices to one another.

12. A method in accordance with claim 8, characterized in that the method is applied to a total fluidic system that has at least one water preparation system, and/or at least one treatment machine, in particular a blood treatment machine, and/or at least one line, in particular a supply line, a loop, a water line, a dialysis line, or a concentrate line.

13. A method in accordance with claim 1, characterized in that a plurality of communication devices are adapted to be arranged in a position in a total fluidic system formed by the devices fluidically connected to one another and to receive and/or transmit non-electric signals, in particular in the form of pressure signals or sound signals, with the non-electric signals being transmitted over a line fluidically connecting to the devices to one another and are arranged at different positions of the total fluidic system.

14. A system for the non-electric communication between devices that are fluidically connected to one another, characterized by at least one communication device in accordance with claim 1 that is arranged at least one position of the total fluidic system and is configured to communicate non-electrically, preferably by means of pressure signals and/or acoustic signals, over at least one line fluidically connecting the devices to one another.

15. A system in accordance with claim 14, characterized in that the system has at least one water preparation systems and/or at least one treatment machine, in particular a blood treatment machine, and/or at least one line, in particular a supply line, a loop, a water line, a dialysis line, or a concentrate line that are fluidically connected and thus preferably form a total fluidic system.

* * * * *